United States Patent [19]
Okamoto

[11] Patent Number: 6,136,169
[45] Date of Patent: Oct. 24, 2000

[54] ABNORMALITY DIAGNOSIS FOR AIR-FUEL RATIO SENSOR SYSTEM

[75] Inventor: Yoshiyuki Okamoto, Kariya, Japan

[73] Assignee: Denso Corporation, Kariya, Japan

[21] Appl. No.: 09/160,549

[22] Filed: Sep. 25, 1998

[30] Foreign Application Priority Data

Oct. 2, 1997 [JP] Japan .................................. 9-269429

[51] Int. Cl.$^7$ .......................... G01N 27/406; F02D 41/02
[52] U.S. Cl. ......................... 204/401; 204/425; 123/688; 123/690
[58] Field of Search ................................. 204/401, 424, 204/425, 426, 427, 428, 429; 123/688, 690

[56] References Cited

U.S. PATENT DOCUMENTS

| | | | |
|---|---|---|---|
| 4,724,814 | 2/1988 | Mieno et al. | 123/688 |
| 4,777,922 | 10/1988 | Mieno et al. | 123/688 |
| 5,709,198 | 1/1998 | Sagisaka et al. | 123/688 |
| 5,833,836 | 11/1998 | Takami et al. | 204/425 |

*Primary Examiner*—Robert J. Warden, Sr.
*Assistant Examiner*—Kaj K. Olsen
*Attorney, Agent, or Firm*—Nixon & Vanderhye P.C.

[57] ABSTRACT

An air-fuel ratio sensor system is diagnosed for the presence/absence of an abnormality on the basis of a reference voltage appearing at one end of a current detecting resistor and a detection voltage appearing at the other end of the current detecting resistor for detecting a current output by an air-fuel ratio sensor. If the reference voltage is outside a normal range and higher than the detection voltage, the air-fuel ratio sensor system is determined to be in a rich abnormality. If the reference voltage Vafon is outside the normal range and lower than the detection voltage, the air-fuel ratio sensor system is determined to be in a lean abnormality. If the reference voltage is within the normal range and a state of the detection voltage being close to a power supply voltage has been continuing for a predetermined period of time, the air-fuel ratio sensor system is determined to be in a circuit-shorting. If the reference voltage is within the normal range and a state of the detection voltage being equal to the reference voltage has been continuing at least for the predetermined period of time, the air-fuel ratio sensor system is determined to be in a circuit-breakage.

16 Claims, 10 Drawing Sheets

ABNORMALITY DIAGNOSIS FOR AIR-FUEL RATIO SENSOR SYSTEM

CROSS REFERENCE TO RELATED APPLICATION

This application relates to and incorporates herein by reference Japanese Patent Application No. 9-269429 filed on Oct. 2, 1997.

BACKGROUND OF THE INVENTION

1. Field of the Invention

The present invention relates to an abnormality diagnosing apparatus and method for an air-fuel ratio sensor system of an internal combustion engine for diagnosing an air-fuel ratio sensor used for detecting an air-fuel ratio of mixture supplied to an engine.

2. Description of Related Art

An air-fuel ratio feedback control system of an internal combustion engine does not function correctly when there is an abnormality in an air-fuel ratio sensor for detecting the air-fuel ratio of air-fuel mixture supplied to the engine. It is thus necessary to detect timely an abnormality occurring in the air-fuel ratio sensor system.

For this reason, JP-A 1-232143 proposes to use a temperature sensor for detecting the temperature of the air-fuel ratio sensor. According to this technology, if the temperature of the air-fuel ratio sensor detected by the temperature sensor does not increase to a predetermined value, a heater for activating the air-fuel ratio sensor is determined to be abnormal. This not only requires a temperature sensor for detecting the temperature of the air-fuel ratio sensor, but also causes a disadvantage that it is impossible to detect failures other than those occurring in the heater.

In addition, JP-A 3-189350 proposes an apparatus for controlling electric power supplied to a heater to adjust the resistance of the heater to a target value. When the amount of electric power supplied to the heater rises beyond a predetermined range, the target value of the heater resistance is determined to be abnormal. The target value of the heater resistance generally becomes abnormal when the battery or the sensor is replaced, that is, during repair work or inspection. Thus, the heater control apparatus is not capable of determining the reliability of the air-fuel ratio sensor in the course of air-fuel ratio feedback control.

Further, JP-A 9-4494 proposes an abnormality diagnosing apparatus. It is, however, impossible to detect a circuit-shorting or a breakage in the air-fuel ratio sensor system in some cases.

SUMMARY OF THE INVENTION

It is thus an object of the present invention to provide an abnormality diagnosing apparatus for an air-fuel ratio sensor system of an internal combustion engine capable of detecting timely a failure caused by a circuit-shorting or a circuit-breakage in an air-fuel ratio sensor system and capable of improving reliability of abnormality diagnoses of the air-fuel ratio sensor system.

According to the present invention, it is determined whether an air-fuel ratio sensor is in an active or inactive state, and an air-fuel ratio sensor system is diagnosed for the presence/absence of an abnormality on the basis of voltages appearing at the ends of a current detecting resistor only when the air-fuel ratio sensor is determined active. This is based on the fact that the voltages appearing at the ends of the current detecting resistor vary in a manner different from a normal operation in the event of a failure caused by an abnormality such as a circuit-shorting and a circuit-breakage occurring in the air-fuel ratio sensor system.

When the air-fuel ratio sensor system is operating normally, the voltage appearing at one end of a current detecting resistor is fixed at a reference voltage and a detection voltage appearing at the other end varies in accordance with a current output by the air-fuel ratio sensor. If the reference voltage appearing at the end of the current detecting resistor has an abnormal value, the air-fuel ratio sensor system can be determined to be abnormal. Thus, when the reference voltage is outside a predetermined range, the air-fuel ratio sensor system is determined to have generated a rich abnormality in which a detected value of the air-fuel ratio is shifted to a rich region or a lean abnormality whereby a detected value of the air-fuel ratio is shifted to a lean region as a diagnosis result based on the reference voltage and the detection voltage. As a result, a lean abnormality and a rich abnormality can be detected with a high degree of precision.

In addition, even when the air-fuel ratio sensor has a circuit-shorting therein, the reference voltage has a value within a normal range, making it impossible to determine an abnormality from the reference voltage. However, the detection voltage is in a state of being pulled up to a level close to a power-supply voltage, no longer varying. Thus, when the reference voltage is within the predetermined range and a state of the detected voltage being pulled up to a level close to a power supply voltage has been continuing for at least a predetermined period of time, the air-fuel ratio sensor system is determined to have a circuit-shorting therein.

In addition, even when the air-fuel ratio sensor has a circuit-breakage therein, the reference voltage has a value within a normal range, making it impossible to determine an abnormality from the reference voltage. However, the detection voltage is equal to the reference voltage in level, no longer varying. Thus, when the reference voltage is within the predetermined range and a state of the detected voltage being equal to the reference voltage in level has been continuing for at least a predetermined period of time, the air-fuel ratio sensor system is determined to have a circuit-breakage therein.

BRIEF DESCRIPTION OF THE DRAWINGS

Other objects, features and advantages of the present invention will become more apparent from the following detailed description made with reference to the accompanying drawings.

DETAILED DESCRIPTION OF THE PREFERRED EMBODIMENTS

First Embodiment

Figure 1:
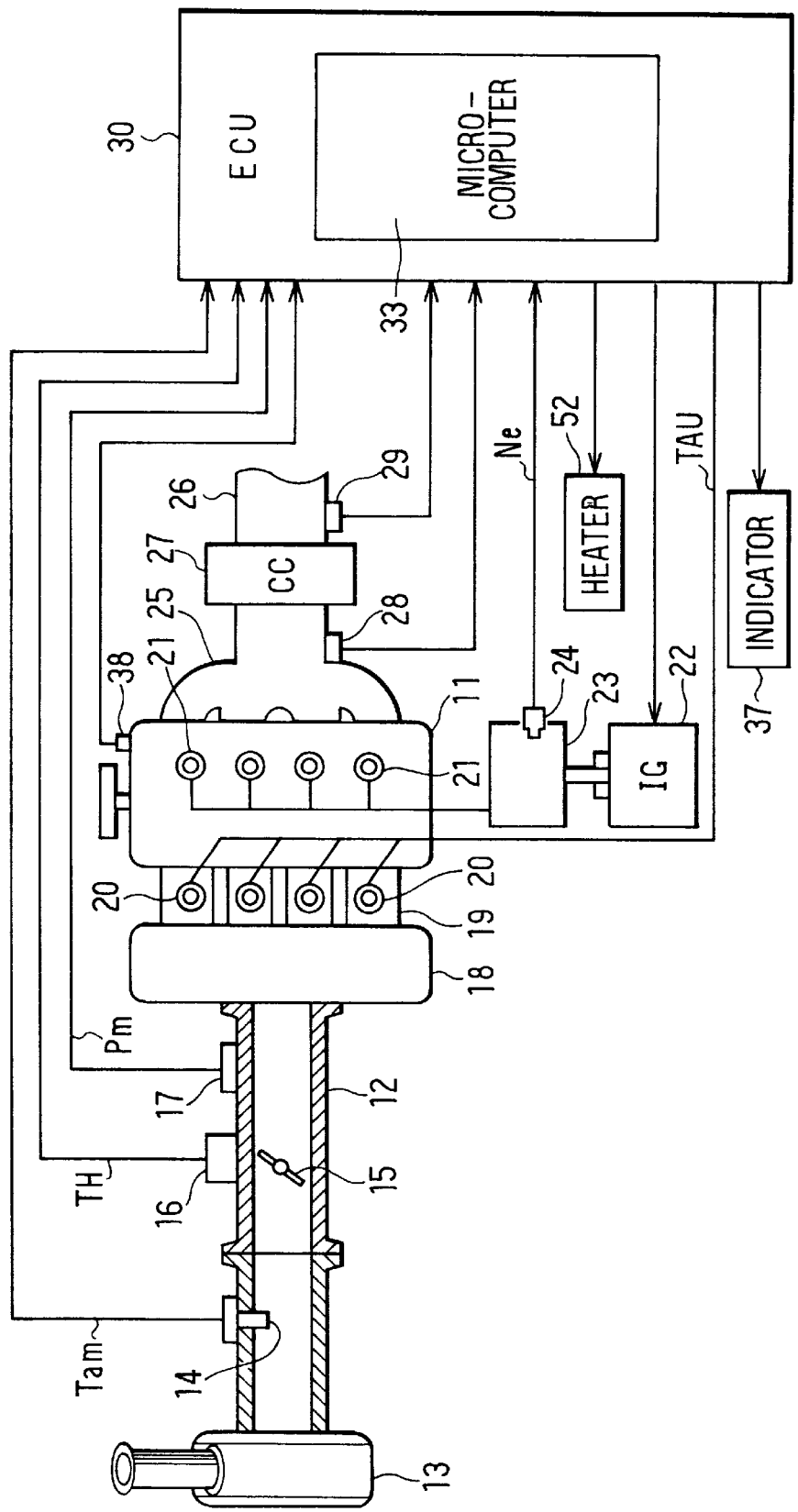
FIG. 1 is a schematic diagram showing an engine control system implementing a first embodiment of the present invention.

A first embodiment of the invention is applied to an engine control system shown in FIGS. 1 to 11. As shown in FIG. 1, at the upmost stream portion of an intake pipe 12 of an internal combustion engine 11, an air cleaner 13 is provided. On the downstream side of the air cleaner 13, an intake air temperature sensor 14 for detecting an intake air temperature Tam is provided. On the downstream side of the intake air temperature sensor 14, a throttle valve 15 and a throttle sensor 16 for detecting a throttle opening angle TH are provided. On the downstream side of the throttle valve 15, an intake air pressure sensor 17 for detecting an intake air pressure PM is provided. On the downstream side of the intake air pressure sensor 17, a surge tank 18 is provided. An intake manifold 19 for introducing air into cylinders of the engine 11 is linked to the surge tank 18. On a branching pipe unit of the intake manifold 19 to the cylinders, injectors 20 for injecting fuel into the respective cylinders are provided.

For each cylinder of the engine 11, an ignition plug 21 is provided. A high voltage current generated by an ignition circuit (IG) 22 is supplied to the ignition plugs 21 by way of a distributor 23. On the distributor 23, there is provided a crank angle sensor 24 for generating typically 24 pulses for each 720 degrees CA (for each two rotations of a crankshaft). An engine revolution speed Ne is detected from intervals between two consecutive pulses generated by the crank angle sensor 24. On the engine 11, a water temperature sensor 38 for detecting an engine coolant water temperature Thw is provided.

On the other hand, an exhaust pipe 26 is connected to an exhaust port of the engine 11 through an exhaust manifold 25. In the middle of the exhaust pipe 26, there is provided a catalyst 27 such as a three-way catalytic converter (CC) for reducing the amount of components such as CO, HC and NOx contained in exhausted gas. On the upstream side of the catalyst 27, there is provided an air-fuel ratio sensor 28 for outputting a limit current which is proportional to the oxygen concentration in the exhaust gas (air-fuel ratio of mixture supplied to the engine). On the downstream side of the catalyst 27, on the other hand, there is provided an oxygen sensor 29 which inverts the output thereof when the air-fuel ratio of the exhausted gas transits from the rich region to the lean region or vice versa.

Figure 2:
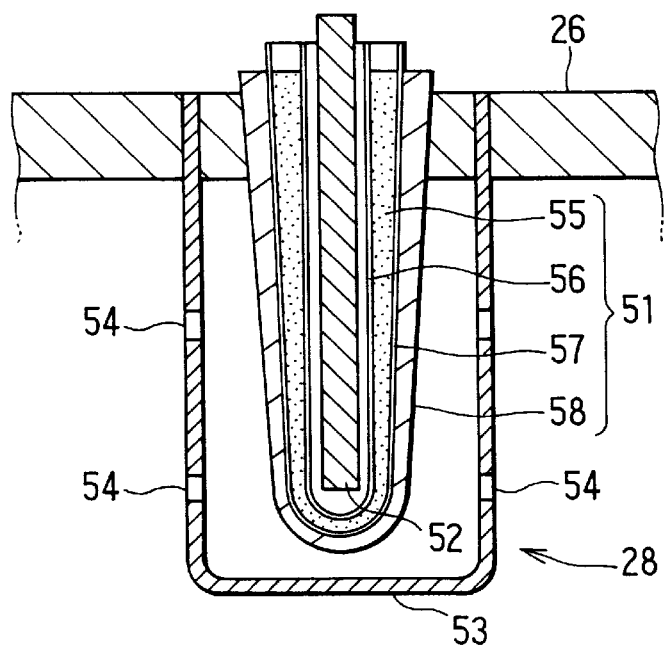
FIG. 2 is a sectional view showing an air-fuel ratio sensor.

As shown in FIG. 2, the air-fuel ratio sensor 28 is installed in a posture, protruding toward the inside of the exhaust pipe 26. The air-fuel ratio sensor 28 comprises a sensor device 51, a heater 52 for heating the sensor device 51 from the inner side and a cover 53 for covering the sensor device 51. The sensor device 51 generates a limit current representing the concentration of oxygen in the lean region of the air-fuel ratio or the concentration of carbon monoxide (CO) in the rich region of the air-fuel ratio. A number of small apertures 54 for flowing in exhausted gas are bored through the peripheral wall of the cover 53.

The sensor device 51 comprises a solid electrolyte layer 55 with a cup-shape, an atmosphere-side electrode layer 56 fixed to the inner surface of the wall of the solid electrolyte layer 55, an exhausted-side electrode layer 57 and a diffusion resistance layer 58 provided on the outer surface of the exhausted-side electrode layer 57 by adopting a plasma spraying technique. The solid electrolyte layer 55 is an oxygen ion conductive oxide sintered body which is made of a material such as $ZrO_2$, $HfO_2$, $ThO_2$ or $Bi_2O_3$ blended with a stabilizer such as CaO, MgO, $Y_2O_3$ or $Yb_2O_3$. The diffusion resistance layer 58 is made of a heat-proof inorganic material such as alumina, magnesia, a quartz rock, spinel or mullite. The exhausted-side electrode layer 57 and the atmosphere-side electrode layer 56 are made of a noble metal with a good catalytic activity such as platinum. The surfaces are coated with a porous chemical plating material. Typically, the area and the width of the exhausted-side electrode layer 57 have a value in the range 10 to 100 square millimeters and a value in the range 0.5 to 2 micrometers respectively. On the other hand, the area and the width of the atmosphere-side electrode layer 56 have a value of at least 10 square millimeters and a value in the range 0.5 to 2.0 micrometers, respectively. The heater 52 is accommodated in the sensor device 51. Energy of heat generated by the heater 52 heats and activates the sensor device 51.

The sensor device 51 generates a variable electromotive force at the stoichiometric air-fuel ratio point, producing a limit current representing the concentration of oxygen in a lean region with respect to the stoichiometric air-fuel ratio point. In this case, the magnitude of the limit current representing the concentration of oxygen is determined by the area of the exhausted-side electrode layer 57 as well as the thickness, the porosity and the average pore diameter of the diffusion resistance layer 58. While the sensor device 51 is capable of linearly detecting the concentration of oxygen, it is necessary to raise the temperature of the sensor device 51 to at least about 650 degrees Celsius in order to activate the sensor device 51. In addition, the activation temperature range of the sensor device 51 is narrow and, with only the heat dissipated by gas exhausted by the engine 11, it is impossible to sufficiently assure a device activation temperature. Therefore, the sensor device 51 is maintained at the activation temperature by heat generated by the heater 52. It should be noted that, in a rich region with respect to the stoichiometric air-fuel ratio point, the concentration of carbon monoxide (CO), unburned gas, changes all but linearly with the air-fuel ratio. For this reason, in the rich region with respect to the stoichiometric air-fuel ratio point, the sensor device 51 generates a limit current representing the concentration of carbon monoxide rather than the concentration of oxygen.

Figure 3:
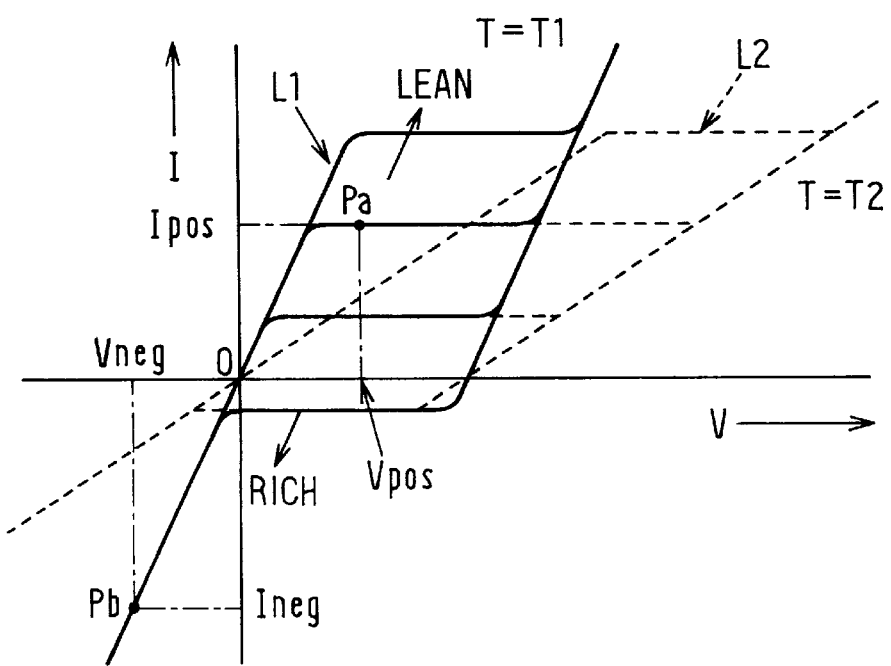
FIG. 3 is a chart showing voltage-current characteristics of the air-fuel ratio sensor.

The voltage-current characteristic of the air-fuel ratio sensor 28 is, as shown in FIG. 3, a linear characteristic representing a relation between a voltage V applied to the solid electrolyte layer 55 and a current I flowing into the solid electrolyte layer 55 which is proportional to a detected concentration of oxygen, that is, the air-fuel ratio. For a temperature T=T1 at which the air-fuel ratio sensor 28 enters an activated state, the relation between the voltage and the current is put in a stable state shown by solid lines L1. In this stable state, straight-line segments of the characteristic line L1 parallel to the voltage axis each represent a limit current. Variations in limit current represent variations in air-fuel ratio, that is, variations in degree of leanness or richness. To be more specific, the more the air-fuel ratio enters the lean side, the greater the magnitude of the limit current and, on the contrary, the more the air-fuel ratio goes to the rich side, the smaller the magnitude of the limit current.

In addition, in the voltage-current characteristic, a region of voltages lower than the straight-line segments parallel to the voltage axis is a resistance dominant region. In the resistance dominant region, the gradient of the characteristic line L1 is determined by the internal resistance of the solid electrolyte layer 55. The internal resistance of the solid electrolyte layer 55 changes with temperature. Specifically, when the temperature of the sensor device 51 decreases, the internal resistance increases with reducing the gradient of the characteristic line L1. That is, when the temperature T of the sensor device 51 is equal to T2 which is lower than T1, the voltage-current characteristic is shifted to a characteristic line L2 shown by dashed lines. Also in this case, straight line segments of the characteristic line L2 parallel to the voltage axis represent limit currents which are generally equal to those of the characteristic line L1.

In the characteristic line L, when a positive voltage Vpos is applied to the solid electrolyte layer 55, a limit current Ipos flows to the sensor device 51. When a negative voltage Vneg is applied to the solid electrolyte layer 55, on the other hand, a temperature current Ineg flows to the sensor device 51 as indicated by a point Pb. The temperature current Ineg is proportional only to the temperature independently of the concentration of oxygen.

Figure 4:
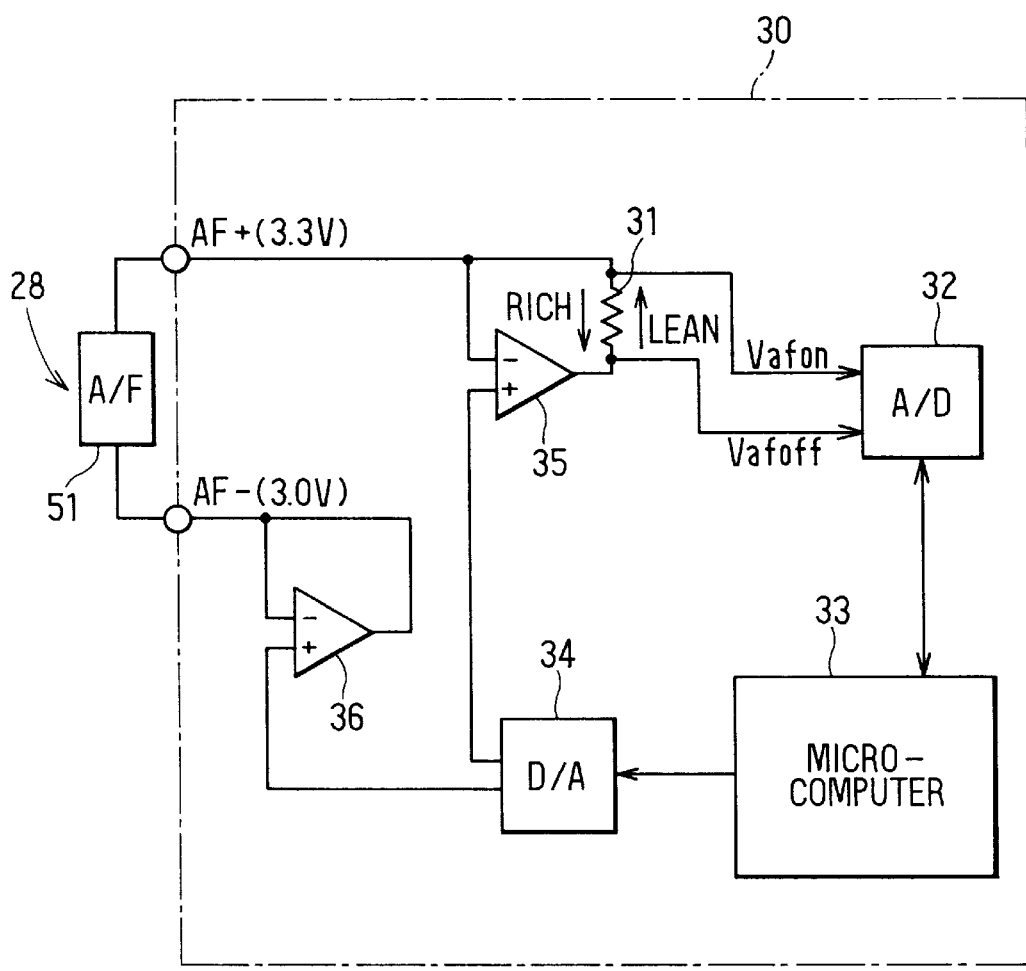
FIG. 4 is a circuit diagram showing an input circuit of the air-fuel ratio sensor.

In FIG. 4 showing a circuit for detecting a value of the air-fuel ratio from a limit current output by the air-fuel ratio sensor 28, two terminals of the sensor device 51 of the air-fuel ratio sensor 28 are connected to terminals AF+ and AF− of the engine control unit (ECU) 30. A reference voltage of typically 3.3 V is applied to the terminal AF+ whereas a voltage of typically 3.0 V is applied to the other terminal AF−. Thus, a voltage of typically 0.3 V is applied across the sensor device 51 of the air-fuel ratio sensor 28.

A current detecting resistor 31 is connected to the terminal AF+ so that the current output by the sensor device 51 flows through the current detecting resistor 31. The voltages Vafon and Vafoff appearing at the two ends of the current detecting resistor 31 are supplied to a microcomputer 33 by way of an A/D converter 32. The microcomputer 33 calculates an air-fuel ratio of exhausted gas from a difference between the voltages Vafon and Vafoff appearing at the two ends of the current detecting resistor 31.

When the air-fuel ratio is in a rich region, the current By flows through the current detecting resistor 31 in a direction opposite to a direction of the current which flows through the current detecting resistor 31 when the air-fuel ratio is in a lean region. At a stoichiometric air-fuel ratio, the current becomes 0, resulting in a voltage Vafon appearing at one end of the current detecting resistor 31 being equal in level to a voltage Vafoff appearing at the other end of the current detecting resistor 31.

It should be noted that the microcomputer 33 outputs a voltage control signal to a D/A converter 34 in order to control the voltage applied to the sensor device 51. The D/A converter 34 outputs control voltages to operational amplifiers 35 and 36 which control voltages applied to the terminals AF+ and AF− to 3.3 and 3.0 V respectively.

The microcomputer 33 inputs signals output by the variety of sensors in addition to the signal output by the air-fuel ratio sensor 28. From the signals, the operating state of the engine 11 is determined. Quantities such as a fuel injection volume TAU and ignition timing Ig appropriate for the operating state of the engine 11 are then determined. Signals representing the fuel injection volume TAU and the ignition timing Ig determined as results of the processing are output to the injectors 20 and the ignition circuit 22. In addition, the microcomputer 33 diagnoses the air-fuel ratio sensor system for the presence/absence of an abnormality occurring therein on the basis of the voltages Vafon and Vafoff appearing at the ends of the current detecting resistor 31. In the event of an abnormality, the microcomputer 33 turns on an indicator light 37 to warn the driver of the abnormality.

Diagnosing the air-fuel ratio sensor system for an abnormality occurring in the air-fuel ratio sensor system is executed as follows.

Figure 5A:
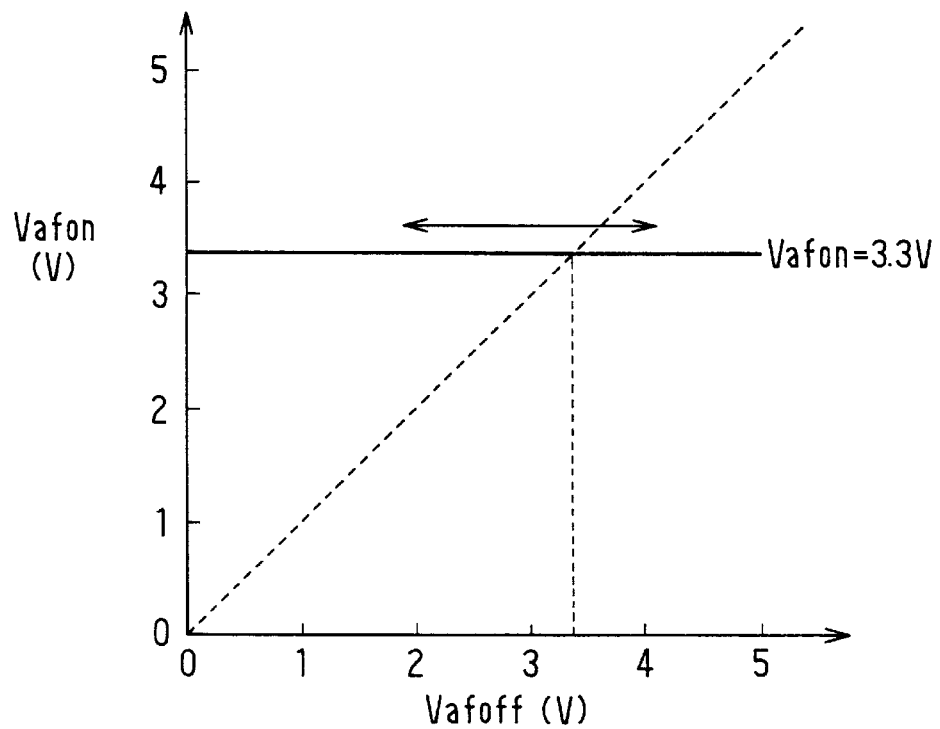
FIGS. 5A and 5B are charts showing relations between variations of voltages Vafon and Vafoff appearing at the ends of a current detecting resistor and variations of an air-fuel ratio A/F in a normal operation of an air-fuel ratio sensor system.
Figure 5B:
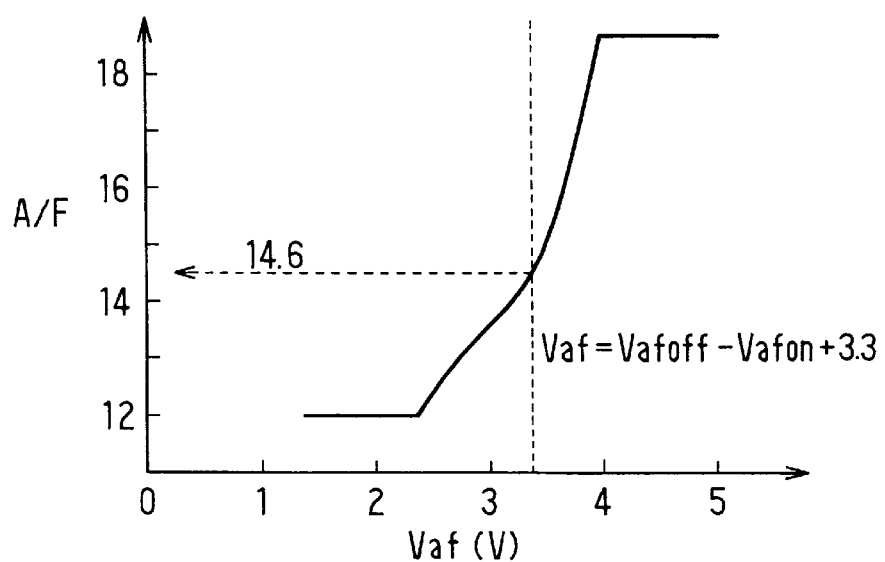
Figure 6:
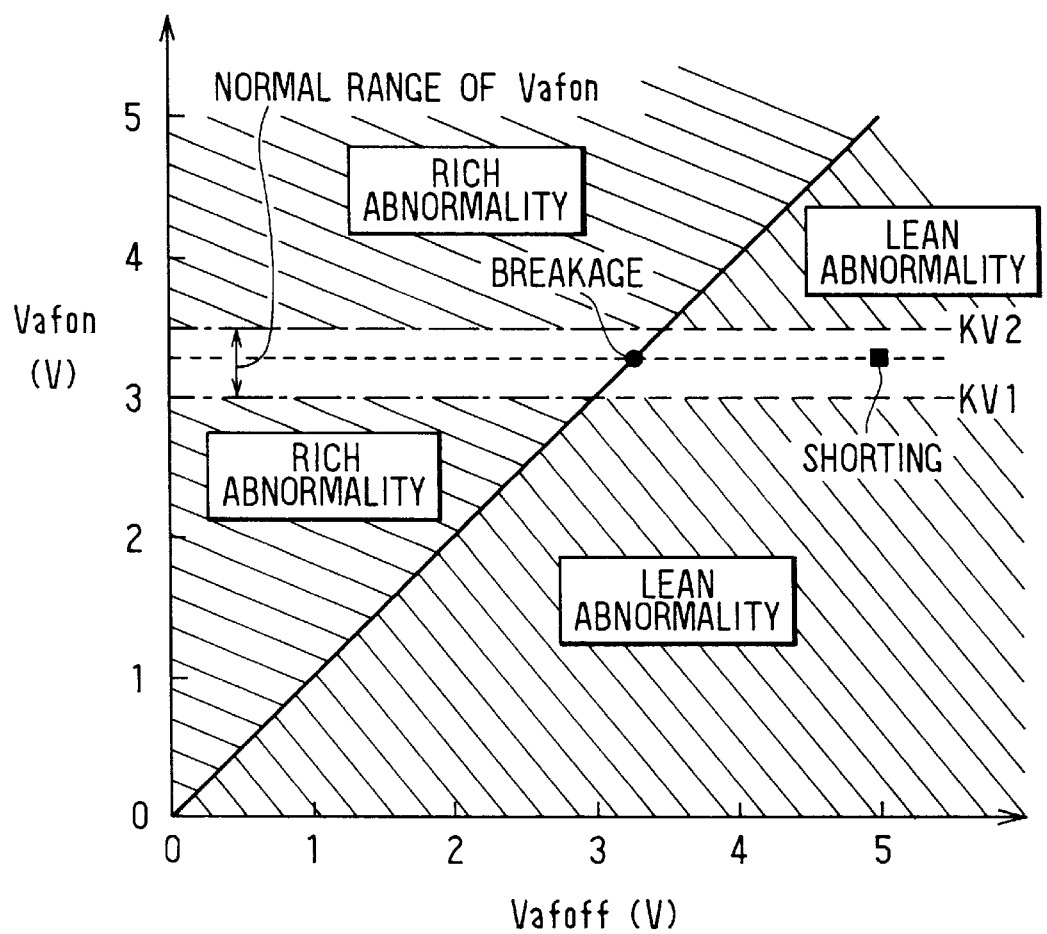
FIG. 6 is a chart showing variations of the voltages Vafon and Vafoff appearing at the ends of the current detecting resistor in an abnormal operation of the air-fuel ratio sensor system.

As shown in FIGS. 5A, 5B and 6, the voltages Vafon and Vafoff appearing at the ends of the current detecting resistor 31 vary in normal and abnormal operations of the air-fuel ratio sensor system. In a normal operation of the air-fuel ratio sensor system, the reference voltage Vafon applied to the terminal of the current detecting resistor 31 is fixed at a value of 3.3 V as shown in FIG. 5A. On the other hand, the voltage Vafoff appearing at the other terminal of the current detecting resistor 31 varies in dependence on the current output by the air-fuel ratio sensor 28. The microprocessor 33 detects the air-fuel ratio A/F from a voltage Vaf computed in accordance with the following equation:

$$Vaf = Vafoff - Vafon + 3.3$$

A relation between the voltage Vaf computed by the above equation and the air-fuel ratio A/F is given by the following table.

| Vaf | 2.4 | 2.5 | 2.6 | 2.7 | 2.8 | 2.9 | 3.0 | 3.1 | 3.2 |
|---|---|---|---|---|---|---|---|---|---|
| A/F | 11.94 | 12.36 | 12.71 | 13.05 | 13.30 | 13.58 | 13.81 | 14.06 | 14.30 |
| Vaf | 3.3 | 3.4 | 3.5 | 3.6 | 3.7 | 3.8 | 3.9 | 4.0 | |
| A/F | 14.60 | 14.99 | 15.43 | 15.995 | 16.56 | 17.14 | 17.82 | 18.52 | |

On the other hand, an abnormality occurring in the air-fuel ratio sensor system can be (1) a rich abnormality, (2) a lean abnormality, (3) a shorting of the sensor device 51, that is, a circuit-shorting of the terminals AF+ and AF− or (4) a breakage of the sensor device 51, that is, a circuit-breakage. The rich abnormality is caused by a detected value of the air-fuel ratio shifted to the rich region. This occurs when the reference voltage Vafon increases to a level above the normal range because the sensor device 51 is shorted to the power supply voltage system (5V). On the other hand, the lean abnormality is caused by a detected value of the air-fuel ratio shifted to the lean region. This occurs when the reference voltage Vafon decreases to a level below the normal range because the sensor device 51 is shorted to the ground.

In the event of a shorting of the sensor device 51 employed in the air-fuel ratio sensor 28, that is, in the event of a shorting of the terminals AF+ and AF−, the reference voltage Vafon is in the normal range so that the abnormality can not be detected from the reference voltage. In this case, however, the reference voltage Vafon is in a state of being pulled up to a level close to the power supply voltage of 5 V and does not change any more.

In the event of a breakage of the sensor device 51, the reference voltage Vafon is also in the normal range so that the abnormality can not be detected from the reference voltage. In this case, however, the reference voltage Vafon is fixed at a level equal to the detection voltage Vafoff and does not change any more.

From the relations between the reference voltage Vafon and the detection voltage Vafoff, the air-fuel ratio sensor system is diagnosed for the presence/absence of an abnormality occurring therein on the basis of the following abnormality diagnosis criteria.

(1) Rich Abnormality

The rich abnormality is defined as a state in which the reference voltage Vafon is beyond the normal range and the reference voltage Vafon is higher than the detection voltage Vafoff.

(2) Lean Abnormality

The lean abnormality is defined as a state in which the reference voltage Vafon is beyond the normal range and the reference voltage Vafon is lower than the detection voltage Vafoff.

(3) Shorting of the Sensor Device between AF+ and AF−

The device shorting abnormality is determined as a state in which the reference voltage Vafon is in the normal range and the detection voltage Vafoff is being pulled up to a level close to the power supply voltage of 5 V, provided that the state has been continuing for at least a predetermined period of time. Abnormalities caused by shorting of the sensor device 51 include an abnormality caused by a circuit-shorting in a harness system as well.

(4) Breakage in the Sensor Device 51

The breakage is determined as a state in which the reference voltage Vafon is in the normal range, having a value equal to the detection voltage Vafoff is determined to be an abnormality caused by a breakage in the sensor device 51, provided that the state has been continuing for at least a predetermined period of time. Abnormalities caused by a breakage in the sensor device 51 include an abnormality caused by a breakage in the harness system as well.

In order to diagnose an air-fuel ratio sensor system for the presence/absence of an abnormality of based on the above criteria (1) to (4), a variety of routines for diagnosing abnormalities shown in FIGS. 7 to 11 are stored in a ROM unit of the microcomputer 33.

Figure 7:
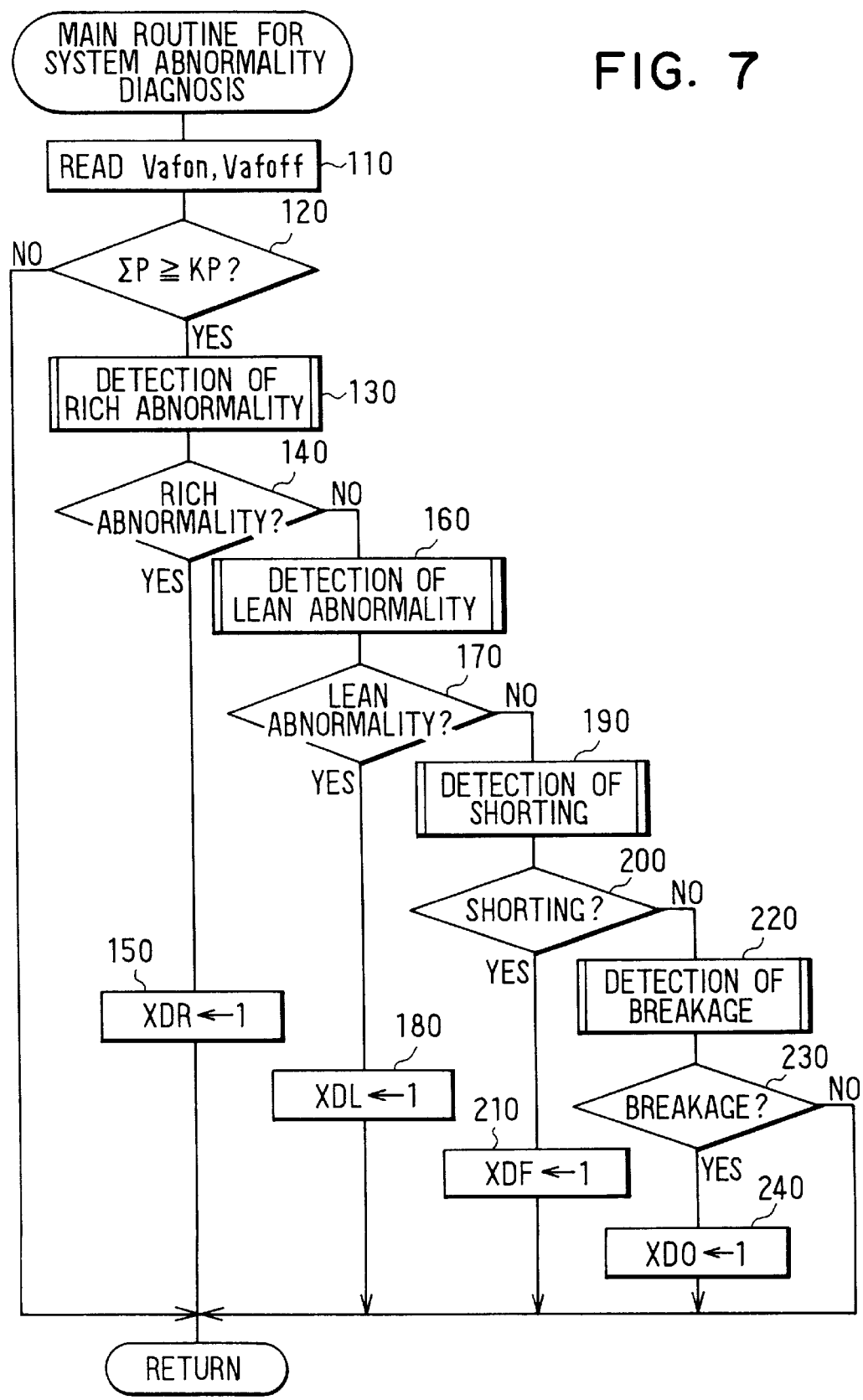
FIG. 7 is a flowchart showing a main routine for diagnosing the air-fuel ratio sensor system abnormality.

A main routine for diagnosing the air-fuel ratio sensor system, shown in FIG. 7, starts at intervals of typically 8 ms, that is, for each A/D conversion of the voltages Vafon and Vafoff appearing at the terminals of the current detecting resistor 31. The main routine starts with step 110 at which the voltages Vafon and Vafoff appearing at the terminals of the current detecting resistor 31 are read in. The routine then determines at step 120 whether a cumulative value ΣP of the electric power supplied to the heater 52 in the air-fuel ratio sensor 28 has reached a predetermined value KP, thereby checking whether the sensor device 51 has been activated.

If the cumulative value ΣP of the electric power supplied to the heater 52 is determined at step 120 to have not reached the predetermined value KP, that is, if the sensor device 51 is determined to have not been activated, the processing is terminated without carrying out the abnormality diagnosis processing.

Figure 8:
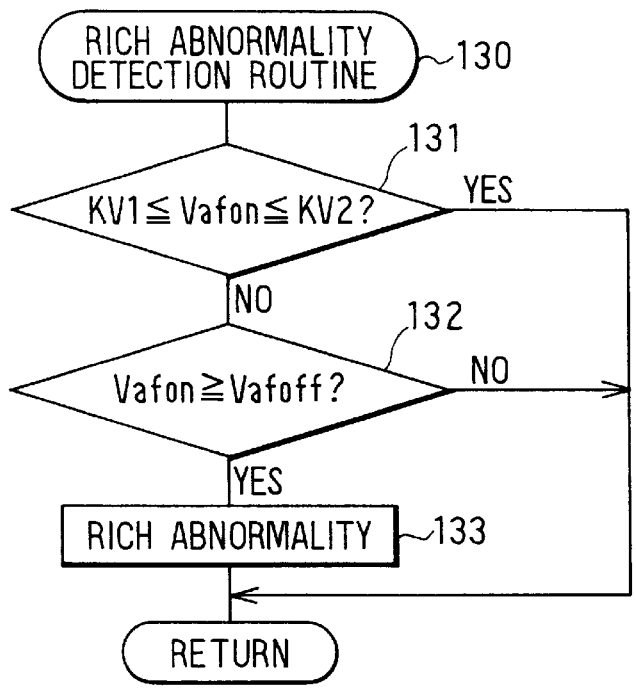
FIG. 8 is a flowchart showing a routine for detecting a rich abnormality.

If the cumulative value ΣP of the electric power supplied to the heater 52 is determined at step 120 to have reached the predetermined value KP, that is, if the sensor device 51 is determined to have been activated, on the other hand, the processing proceeds to step 130 at which a rich abnormality detecting routine shown in FIG. 8 is executed. As shown in the figure, the rich abnormality routine begins with step 131 to determine whether the reference voltage Vafon is in a normal range, that is, KV1≦Vafon≦KV2. Since a value of the reference voltage Vafon in the normal range indicates that no rich abnormality has occurred, the processing is finished immediately. If the reference voltage Vafon is outside the normal range, that is, for Vafon<KV1 or Vafon>KV2, on the other hand, the processing continues to step 132 to determine whether the reference voltage is at least equal to the detection voltage Vafoff, that is, Vafon≧Vafoff. If the reference voltage is determined lower than the detection voltage Vafoff, the processing is finished.

If the reference voltage Vafon is determined to be at least equal to the detection voltage Vafoff, on the other hand, the processing goes on to step 133 at which the processing is finished with the condition for a rich abnormality determined to be satisfied. The processing then returns to step 140 of the main routine shown in FIG. 7. If the condition for a rich abnormality is determined to be satisfied at step 140, the processing proceeds to step 150 at which a rich abnormality flag XDR is set to 1 to indicate that a rich abnormality has occurred.

Figure 9:
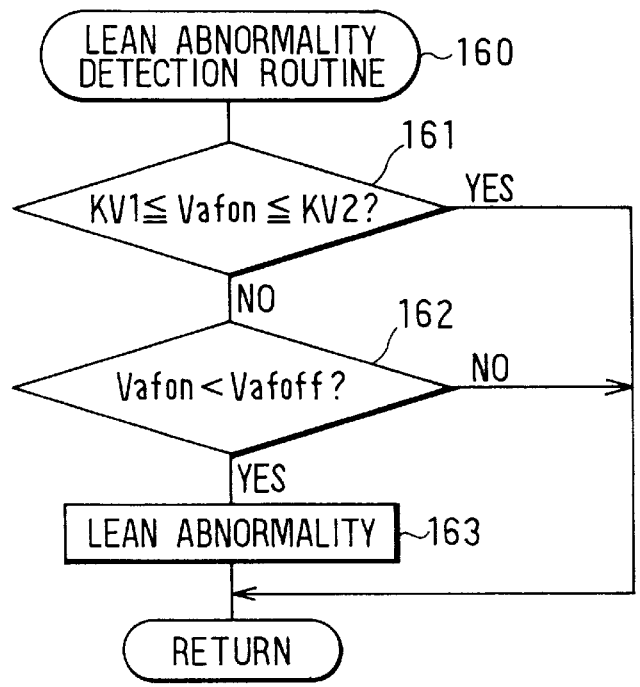
FIG. 9 is a flowchart showing a routine for detecting a lean abnormality.

If the condition for a rich abnormality is determined to be not satisfied at step 140, on the other hand, the processing proceeds to step 160 at which a lean abnormality detecting routine shown in FIG. 9 is executed. As shown in the figure, the lean abnormality routine begins with step 161 to determine whether the reference voltage Vafon is within the normal range, that is, KV1≦Vafon≦KV2. Since a value of the reference voltage Vafon in the normal range indicates that no lean abnormality has occurred, the processing is finished immediately. If the reference voltage Vafon outside the normal range, that is, for Vafon<KV1 or VAFon>KV2, on the other hand, the processing continues to step 162 to determine whether the reference voltage Vafon is lower than the detection voltage Vafoff, that is, Vafon<Vafoff. If the reference voltage is determined to be at least equal to the detection voltage Vafoff, the processing is finished.

If the reference voltage Vafon is determined to be lower than the detection voltage Vafoff, on the other hand, the processing goes on to step 163 at which the processing is finished with the condition for a lean abnormality determined to be satisfied. The processing then returns to step 170 of the main routine shown in FIG. 7. If the condition for a lean abnormality is determined to be satisfied at step 170, the processing proceeds to step 180 at which a lean abnormality flag XDL is set to 1 to indicate that the lean abnormality has occurred.

Figure 10:
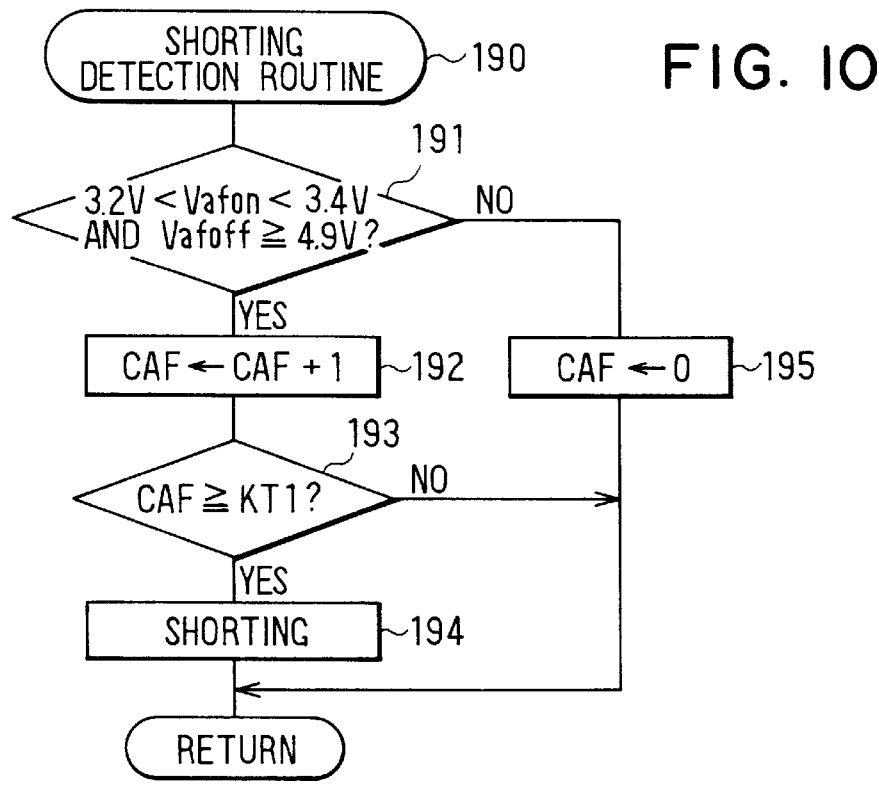
FIG. 10 is a flowchart showing a routine for detecting a circuit-shorting in a sensor device.

If the condition for a lean abnormality is determined to be not satisfied at step 170, on the other hand, the processing proceeds to step 190 at which a sensor device shorting detecting routine shown in FIG. 10 is executed. As shown in the figure, the sensor device shorting detecting routine begins with step 191 to determine whether 3.2 V<Vafon<3.4 V and Vafoff≧4.9 V. If these conditions are determined to be unsatisfied, no sensor device shorting, that is, no shorting between the terminals AF+ and AF−, is detected. In this case, the processing goes on to step 195 at which an abnormal state continuation time counter CAF is reset to 0.

If the conditions 3.2 V<Vafon<3.4 V and Vafoff≧4.9 V are determined at step 191 to be both satisfied, on the other hand, the processing proceeds to step 192 at which the contents of the counter CAF are incremented. Then, the processing continues to step 193 to determine whether the contents of the counter CAF are at least equal to a predetermined value KT1 typically in the range 5 to 10 seconds. If the contents of the counter CAF are determined smaller than the predetermined to be value KT1, the processing is finished. If the contents of the counter CAF are determined to be at least equal to the predetermined value KT1, on the other hand, the processing is finished with the condition for a sensor device shorting satisfied. The processing then returns to step 200 of the main routine shown in FIG. 7. If the condition for a sensor device shorting is determined to be satisfied at step 200, the processing proceeds to step 210 at which a sensor device shorting flag XDF is set to 1 to indicate that the sensor device shorting has been detected.

Figure 11:
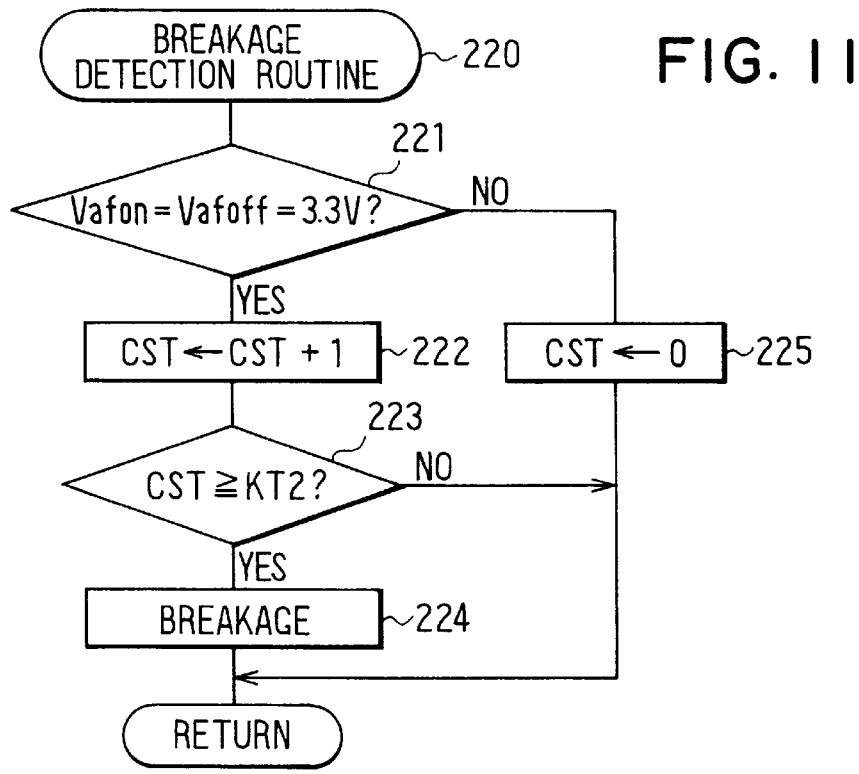
FIG. 11 is a flowchart showing a routine for detecting a circuit-breakage in a sensor device.

If the condition for a sensor device shorting is determined to be not satisfied at step 200, on the other hand, the processing proceeds to step 220 at which a sensor device breakage detecting routine shown in FIG. 11 is executed. As shown in the figure, the sensor device breakage detecting routine begins with step 221 to determine whether Vafon=Vafoff=3.3 V. This step 221 also determines that the reference voltage Vafon is within the predetermined voltage range, because 3.3 V is within the range of 3.2 V to 3.4 V. If this condition is not satisfied, no sensor device breakage is determined to exist. In this case, the processing goes on to step 225 at which an abnormality state continuation time counter CST is reset to 0 and this processing is finished.

If Vafon=Vafoff=3.3 V is determined at step 221 to hold true, on the other hand, the processing proceeds to step 222 at which the contents of the counter CST are incremented. Then, the processing continues to step 223 to determine whether the contents of the counter CST are at least equal to a predetermined value KT2 typically in the range 5 to 10 seconds. If the contents of the counter CST are determined to be smaller than the predetermined value KT2, the processing is finished. If the contents of the counter CST are determined to be at least equal to the predetermined value KT2, on the other hand, the processing is finished with the condition for a sensor device breakage satisfied. The processing then returns to step 230 of the main routine shown in FIG. 7. If the condition for a sensor device breakage is determined to be satisfied at step 230, the processing proceeds to step 240 at which a sensor device breakage flag XDO is set to 1 to indicate that the sensor device breakage has been detected.

If the condition for the sensor device breakage is determined to be unsatisfied at step 230, on the other hand, the air-fuel ratio sensor system is finally diagnosed to be normal, thus finishing the main routine.

According to the first embodiment described above, the air-fuel ratio sensor system is diagnosed for an abnormality on the basis of the voltages Vafon and Vafoff appearing at the two ends of the current detecting resistor 31. As a result, a failure such as a shorting and a breakage in the sensor device 51 that can not be detected by the conventional abnormality detecting apparatus can now be detected timely, allowing the reliability of abnormality diagnoses of the air-fuel ratio sensor system to be improved.

Figure 12:
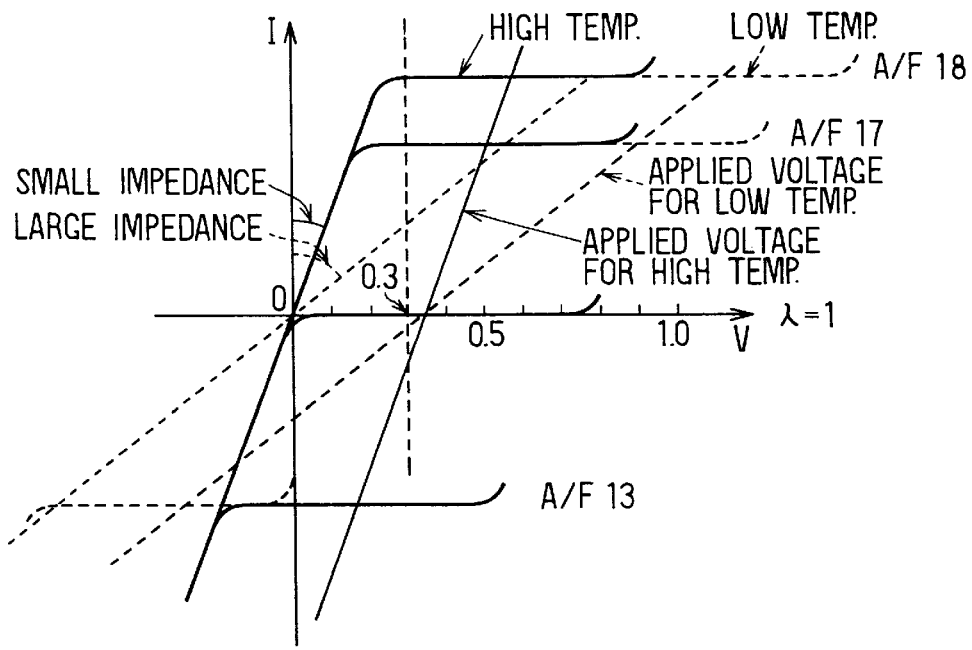
FIG. 12 is a chart showing relations among a voltage-current characteristic, a device temperature, a device impedance and an applied voltage of the air-fuel ratio sensor.

In the first embodiment described above, the voltage applied to the sensor device 51 in the air-fuel ratio sensor 28 is fixed at 0.3 V. However, if the temperature of the sensor device 51 in the air-fuel ratio sensor 28 decreases, the device impedance increases, reducing the current (device current) flowing through the sensor device 51 as shown in FIG. 12. The temperature of the sensor device 51 is referred to as a device temperature. Thus, the detection values of the air-fuel ratio sensor 28, namely, the voltages Vafon and Vafoff appearing at the two ends of the current detecting resistor 31, are affected by the device temperature.

Second Embodiment

Figure 13:
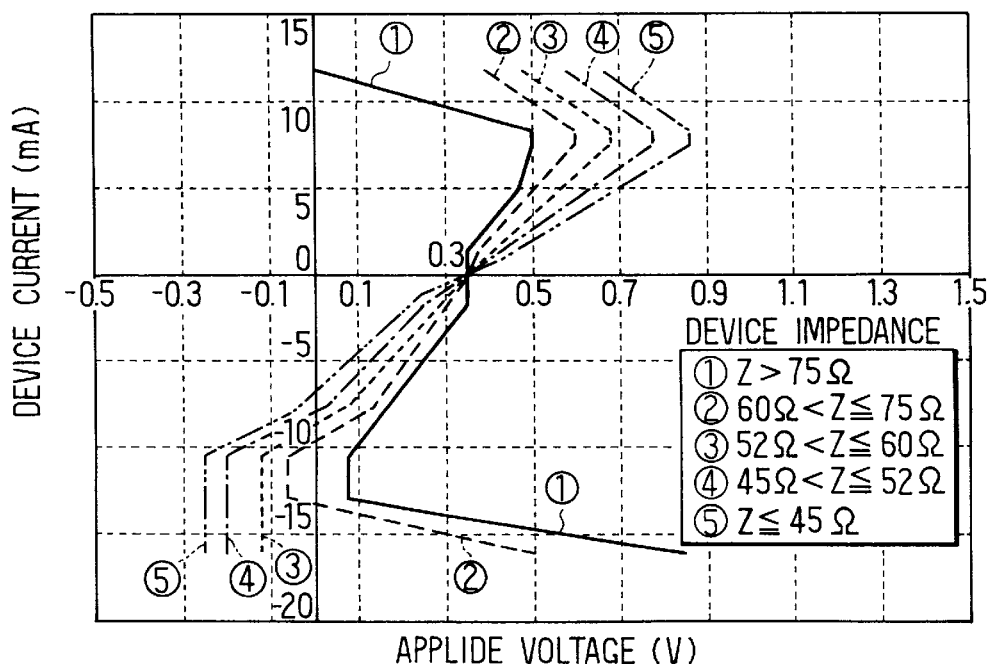
FIG. 13 is a chart showing characteristics of variations in applied voltage according to a second embodiment.

In order to cope with this problem, in a second embodiment, the microcomputer 33 changes the voltage applied to the sensor device 51 in accordance with the device impedance, which depends on the device temperature, and the device current as shown in FIG. 13. In this way, variations in device current caused by changes in device temperature can be canceled by altering the voltage applied to the sensor device 51. As a result, the air-fuel ratio can be detected with a high degree of precision without being affected by changes in device temperature.

Figure 14:
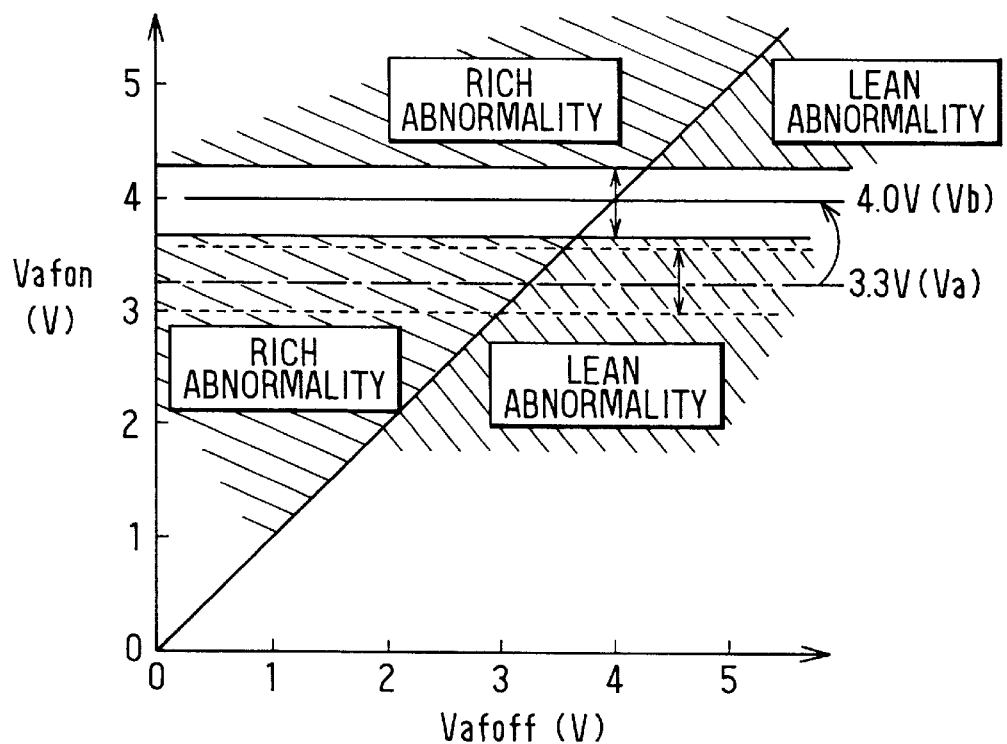
FIG. 14 is a chart showing a relation among a reference voltage, a detection voltage and an abnormality which is obtained when the applied voltage is changed.

If the reference voltage is changed from Va of 3.3 V to Vb of 4.0 V as shown in FIG. 14, for example, the abnormality determination criterion values used at steps 131 and 161 of the routines shown in FIGS. 8 and 9 are changed from KV1 and KV2 to KV1+(Vb−Va) and KV2+(Vb−Va), respectively. In addition, at step 191 in the routine shown in FIG. 10, the microcomputer 33 determines whether the following conditions are satisfied:

$$3.2V+(Vb-Va)<Vafon<3.4V+(Vb-Va),$$

and $$Vaoff \geq 4.9V$$

Furthermore, at step 221 in the routine shown in FIG. 11, the microcomputer 33 determines whether the following condition is satisfied:

$$Vafon=Vafoff=3.3+(Vb-Va)$$

The remaining processing of the second embodiment may be the same as the first embodiment. In the second embodiment, the abnormality determination criterion values are changed in accordance with a variation in voltage applied to the sensor device 51. As a result, the air-fuel ratio can be detected with a high degree of precision without being affected by changes in voltage applied to the sensor device 51.

Third Embodiment

Figure 15:
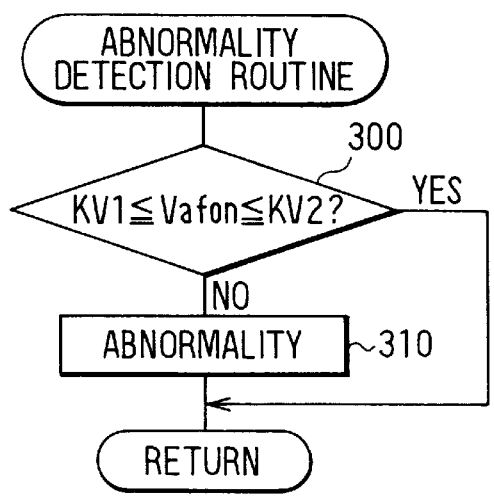
FIG. 15 is a flowchart showing a routine for diagnosing the air-fuel ratio sensor system for an abnormality according to a third embodiment.

In a third embodiment, the air-fuel ratio sensor system is diagnosed for an abnormality on the basis of the reference voltage only. As shown in FIG. 15, the processing begins with step 300 to determine whether the reference voltage Vafon is within a predetermined range with a lower voltage limit KV1 and an upper voltage limit KV2, that is, whether the reference voltage is at least equal to a lower voltage limit KV1 and does not exceed an upper voltage limit KV2. This is because, since the reference voltage normally has a fixed value, only in the event of an abnormality such as a shorting of battery terminals does the reference voltage go beyond the predetermined range. Thus, a result of the determination of step 300 indicating that the reference voltage Vafon is within the predetermined range implies that there is no abnormality. In this case, the processing is finished. On the other hand, a result of the determination of step 300 indicating that the reference voltage is beyond a predetermined range indicates that there is an abnormality. In this case, the processing goes on to step 310 at which the condition for the detection of an abnormality is established. Thus, an abnormality can be determined with ease by merely checking the reference voltage Vafon appearing at one end of the current detecting resistor 31.

Fourth Embodiment

Figure 16:
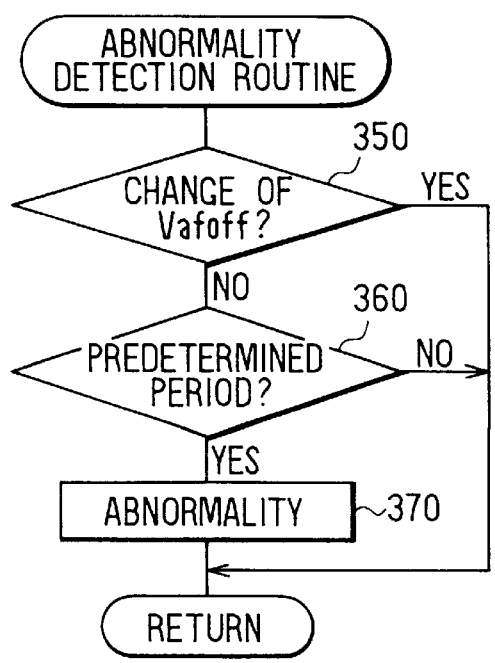
FIG. 16 is a flowchart showing a routine for diagnosing the air-fuel ratio sensor system for an abnormality according to a fourth embodiment.

In a fourth embodiment, as shown in FIG. 16, diagnosing the air-fuel ratio sensor system for an abnormality is executed on the basis of the detection voltage only. That is, the processing begins with step 350 to determine whether the detection voltage Vafoff has changed from a value obtained in an immediately preceding operation. The detection voltage Vafoff different from the immediately preceding one indicates that there is no abnormality occurring in the air-fuel ratio sensor system. In this case, the processing is finished. If the detection voltage Vafoff is determined unchanged from the immediately preceding one, on the other hand, the processing goes on to step 360 to determine whether the state of detection voltage being unchanged from the preceding one has been continuing for at least a predetermined period of time. If the result of the determination indicates that the state has not been continuing for the predetermined period of time, the air-fuel ratio sensor system is determined to be normal. If the result of the determination indicates that the state has been continuing for the predetermined period of time, on the other hand, the processing proceeds to step 370 at which the air-fuel ratio sensor system is determined to be abnormal.

This is because, since the concentration of oxygen in the exhausted gas always changes, an unchanging detection voltage produced by the current detecting resistor 31 in spite of the ever changing air-fuel ratio indicates that an abnormality has occurred in the air-fuel ratio sensor system for some reasons.

The third and the fourth embodiments may be implemented singly or in combination.

The present invention should not be limited to the above embodiments, but may be changed or modified without departing from the spirit of the invention.

What is claimed is:

1. An abnormality diagnosing apparatus for an air-fuel ratio sensor system of an internal combustion engine which detects an air-fuel ratio of mixture by flowing a current of an air-fuel ratio sensor through a current detecting resistor and detecting a difference between two voltages appearing at both ends of the current detecting resistor, the abnormality diagnosing apparatus comprising:

activation determining means for determining whether the air-fuel ratio sensor is in an active state; and abnormality diagnosing means for diagnosing the air-fuel ratio sensor system for a presence/absence of at abnormality from a combination of results of predetermined comparison processings made separately with respect to each of the voltages appearing at the ends of the current detecting resistor, only when the air-fuel ratio sensor is determined to be in the active state.

2. An abnormality diagnosing apparatus as in claim 1, wherein:

the voltage appearing at one end of the current detecting resistor is a reference voltage, and the voltage appearing at the other end of the current detecting resistor is a detection voltage varying in accordance with the current of the air-fuel ratio sensor; and the abnormality diagnosing means determines, when the reference voltage is outside a predetermined range, a rich abnormality in which a detected value of the air-fuel ratio is shifted to a rich region and a lean abnormality in which the detected value of the air-fuel ratio is shifted to a lean region, based on the reference voltage and the detection voltage.

3. An abnormality diagnosing apparatus as in claim 2, wherein:

the abnormality diagnosing means determines that the lean abnormality has occurred when the reference voltage is outside the predetermined range and the reference voltage is lower than the detection voltage.

4. An abnormality diagnosing apparatus as in claim 2, wherein:

the abnormality diagnosing means determines that the rich abnormality has occurred when the reference voltage is outside the predetermined range and the reference voltage is higher than the detection voltage.

5. An abnormality diagnosing apparatus as in claim 2, wherein:

the abnormality diagnosing means determines an occurrence of a circuit-shorting, when the reference voltage is within the predetermined range and a state of the detection voltage being pulled up to a level close to a power supply voltage has been continuing for at least a predetermined period of time.

6. An abnormality diagnosing apparatus as in claim 2, wherein:

the abnormality diagnosing means determines an occurrence of circuit-breakage in the air-fuel ratio sensor system, when the reference voltage is within the predetermined range and a state of the detection voltage being equal to the reference voltage in level has been continuing for at least a predetermined period of time.

7. An abnormality diagnosing apparatus as in claim 2, further comprising:

applied voltage changing means for changing a voltage applied between terminals of the air-fuel ratio sensor in accordance with a device impedance or a device temperature, wherein the abnormality diagnosing means changes the reference voltage for determining an abnormality in accordance with a change in the applied voltage.

8. An abnormality diagnosing apparatus for an air-fuel ratio sensor system of an internal combustion engine which detects an air-fuel ratio of mixture by flowing a current of an air-fuel ratio sensor through a current detecting resistor and detecting a difference between voltages appearing at ends of the current detecting resistor the abnormality diagnosis apparatus comprising:

activation determining means for detecting an active state of the air-fuel ratio sensor; and abnormality diagnosing means for diagnosing the air-fuel ratio sensor system for a presence/absence of abnormality on the basis of a voltage which appears at least one of the ends of the current detecting resistor, only when the air-fuel ratio sensor is determined to be in the active state, wherein the voltage appearing at one end of the current detecting resistor is a reference voltage and the voltage appearing at the other end of the current detecting resistor is a detection voltage varying in accordance with the current of the air-fuel ratio sensor; and the abnormality diagnosing means determines the air-fuel ratio sensor system to be abnormal when the reference voltage is outside a predetermined range.

9. An abnormality diagnosing apparatus for an air-fuel ratio sensor system of an internal combustion engine which detects an air-fuel ratio of mixture by flowing a current of an air-fuel ratio sensor through a current detecting resistor and detecting a difference between voltages appearing at ends of the current detecting resistor the abnormality diagnosis apparatus comprising:

activation determining means for detecting an active state of the air-fuel ratio sensor; and abnormality diagnosing means for diagnosing the air-fuel ratio sensor system for a presence/absence of abnormality on the basis of a voltage which appears at at least one of the ends of the current detecting resistor, only when the air-fuel ratio sensor is determined to be in the active state, wherein the voltage appearing at one end of the current detecting resistor is a reference voltage and the voltage appearing at the other end of the current detecting resistor is a detection voltage varying in accordance with the current of the air-fuel ratio sensor; and the abnormality diagnosing means determines the air-fuel ratio sensor system to be abnormal when a state of the detection voltage being unchanged continues for a predetermined period of time.

10. An abnormality diagnosing apparatus for an air-fuel ratio sensor system of an internal combustion engine, comprising:

a current detecting resistor through which a current of an air-fuel ratio sensor of said air-fuel ration sensor system flows; and a processing circuit configured to measure voltages at each end of the current detecting resistor, to separately apply abnormality diagnosis criteria with respect to each of the measured voltages and to detect a presence/absence of an abnormality of said air-fuel ratio sensor system based on the results of the applied abnormality diagnosis criteria.

11. An abnormality diagnosing apparatus as in claim 10, wherein:

the voltage detected at one end of said current detecting resistor is a reference voltage and the voltage detected at the other end of said current detecting resistor is a detection voltage that varies in accordance with the current flowing through said air-fuel ratio sensor.

12. An abnormality diagnosing apparatus as in claim 11, wherein:

said processing circuit detects a rich abnormality in which the air-fuel ratio is shifted to a rich region by applying one criterion to determine whether the reference voltage is outside a predetermined range and applying another criterion to determine whether the reference voltage is greater than the detection voltage.

13. An abnormality diagnosing apparatus as in claim 11, wherein:

said processing circuit detects a lean abnormality in which the air-fuel ratio is shifted to a lean region by applying one criterion to determine whether the reference voltage is outside a predetermined range and applying another criterion to determine whether the reference voltage is less than the detection voltage.

14. An abnormality diagnosing apparatus as in claim 11, wherein:

said processing circuit detects a short-circuit by applying one criterion to determine whether the reference voltage is within a predetermined range and applying another criterion to determine whether a level of the detection voltage is close to a power supply voltage for at least a predetermined period of time.

15. An abnormality diagnosing apparatus as in claim 11, wherein:

said processing circuit detects a circuit breakage in the air-fuel ratio sensor system by applying one criterion to determine whether the reference voltage is within a predetermined range and applying another criterion to determine whether a level of the detection voltage is equal to a level of the reference voltage for at least a predetermined period of time.

16. An abnormality diagnosing apparatus as in claim 10, wherein:

said processing circuit is further configured to adjust the applied abnormality diagnosis criteria in accordance with changes in a voltage applied across said air-fuel sensor.

* * * * *